United States Patent [19]

Bernt et al.

[11] 4,080,263

[45] Mar. 21, 1978

[54] PROCESS AND REAGENT FOR THE RAPID QUANTITATIVE DETERMINATION OF LACTATE OR ALANINE

[75] Inventors: Erich Bernt; Peter Scheibe, both of Munich; Ingeborg Gutmann, Percha uber Starnberg, all of Germany

[73] Assignee: Boehringer Mannheim GmbH, Mannheim-Waldhof, Germany

[21] Appl. No.: 713,472

[22] Filed: Aug. 11, 1976

[51] Int. Cl.² ............................................. G01N 31/14
[52] U.S. Cl. .................................. 195/99; 195/103.5 R
[58] Field of Search ................... 195/99, 101, 103.5 R, 195/114, 111; 23/230 B, 230 R; 252/408 R

[56] References Cited

U.S. PATENT DOCUMENTS

| 3,413,198 | 11/1968 | Deutsch et al. | 195/103.5 R |
| 3,573,171 | 3/1971 | Green et al. | 195/103.5 R |
| 3,778,350 | 12/1973 | Bergmeyer et al. | 195/103.5 C |

OTHER PUBLICATIONS

Bergmeyer et al., *Methods of Enzymatic Analysis*, vol. 3, Academic Press Inc., New York, San Francisco, London, (1974), pp. 1468-1479.

Bergmeyer, *Methods of Enzymatic Analysis*, Academic Press, New York and London, (1965), pp. 378-380.

*Primary Examiner*—Raymond N. Jones
*Assistant Examiner*—Thomas G. Wiseman
*Attorney, Agent, or Firm*—Burgess, Dinklage & Sprung

[57] ABSTRACT

L-lactate is quantitatively determined by the reaction thereof with nicotinamide-adenine-dinucleotide (NAD) in the presence of lactate dehydrogenase (LDH) with the formation of reduced NAD (NADH) and pyruvate, reaction of the latter with glutamate in the presence of glutamate-pyruvate-transaminase (GPT) with the formation of alanine and α-ketoglutarate in alkaline buffered solution and measurement of the NADH formed, wherein the reaction is carried out in the presence of at least 0.4 mol/liter of carbonate or bicarbonate.

8 Claims, No Drawings

PROCESS AND REAGENT FOR THE RAPID QUANTITATIVE DETERMINATION OF LACTATE OR ALANINE

The present invention is concerned with a process and reagent for the quantitative determination of lactate.

The determination of lactate in blood, serum or plasma is important for the adjustment and therapy control of diabetics. Increased lactate contents also occur in cases of shock, myocardial infarct, uraemia, leukaemia and cirrhosis of the liver. Therefore, the determination of lactate is of diagnostic importance.

Various methods are already known for the specific determination of L-lactate. They depend upon the conversion of the lactate into pyruvate in the presence of lactatedehydrogenase (LDH) and of the co-enzyme nicotinamideadenine-dinucleotide (NAD), with the reduction of the latter to give NADH. The NADH formed can be determined optically either directly or through the intermediary of a redox dyestuff.

However, in many cases, the determination of L-lactate is of clinical importance for an emergency investigation in which the shortest possible determination times are necessary. Thus, for example, in the case of the biguanide therapy of diabetes mellitus, a lactacidosis can occur which can be fatal. For such cases, the rapid determination of lactate is an urgent necessity.

A disadvantage of the above-described known process using LDH is the fact that the determination takes a substantial period of time which, in general, is more than one hour since it is necessary to measure against the chemical equilibrium of the reaction catalyzed by the LDH.

Therefore, various attempts have been made to shorten the period of time needed for carrying out the determination. Thus, it is known from German Patent Specification No. 1,944,911 to follow the above-described reaction by a second reaction in which the pyruvate formed is reacted with glutamate in the presence of glutamatepyruvate-transaminase (GPT), with the formation of alanine and α-ketoglutarate. In this way, the chemical equilibrium is improved but the measurement still takes more than half an hour and is, therefore, not suitable for an emergency investigation.

Other known suggestions have the object of displacing the equilibrium by the addition of hydrazine as ketone receptor or of replacing the NAD by acetylpyridine-adeninedinucleotide (APAD) (see H. U. Bergmeyer, Methoden der enzymatischen Analyse, pub. Verlag Chemie, Weinheim, Vol. II, pages 1510–1526/1974). An attempt has also been made to use LDH from bovine heart and to increase the temperature to 45° C. (see Klin. Biochem., 7, 94/1974).

However, a common disadvantage of all of these processes is that the reduction of the period of determination is not sufficient to satisfy the clinical requirements and, hence, there has been a need for a more rapid method.

The present invention provides a process for the quantitative determination of lactate which requires a substantially shortened period of time and preferably requires, at most, 10 minutes for the determination.

The process of the invention comprises the quantitative determination of L-lactate by the reaction thereof with nicotinamide-adenine-dinucleotide (NAD) in the presence of lactate dehydrogenase (LDH) with the formation of reduced NAD (NADH) and pyruvate, reaction of the latter with glutamate in the presence of glutamate-pyruvate-transaminase (GPT) with the formation of alanine and α-ketoglutarate in alkaline buffered solution and measurement of the NADH formed, wherein the reaction is carried out in the presence of at least 0.4 mol/liter of carbonate or bicarbonate.

The present invention is based on the surprising discovery that carbonate and bicarbonate ions are able, at certain relatively high concentrations, to considerably activate glutamate-pyruvate-transaminase and thereby to make possible a considerable displacement of the equilibrium in the combined reaction with LDH and GPT.

In the above-mentioned German Patent Specification No. 1,944,911, a reagent for the determination of lactate has admittedly already been described which can also contain bicarbonate or carbonate. However, the given concentrations are 0.1 mol/liter or lower and thus in a range in which no activation takes place. An indication of the possibility of an activation at substantially higher concentrations of these compounds could not be deduced therefrom.

The following reactions form the basis of the process according to the present invention:

1. 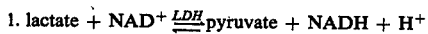

2. 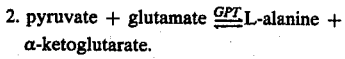

Since, according to reaction 1, hydrogen ions are formed, the process is carried out in an alkaline medium.

In the case of the process according to the present invention, it is preferable to work in 0.45 to 1.0 mol/liter carbonate buffer. In this case, pH values of from 9.5 to 10.5 have proved to be especially favorable, whereas hitherto the coupled reaction with LDH and GPT has been carried out at pH 8.9.

The process according to the present invention can be carried out not only with whole blood after deproteinization with, for example, perchloric acid, but also with serum or plasma.

The process according to the present invention can be carried out by adding deproteinized blood, serum or plasma to the reagent mixing which contains all the reagents apart from the enzymes. The batch is thereafter divided into two equal halves. The enzymes are added to one half and the second half serves as a blank. After 10 minutes, the extinction is measured in the sample and in the blank. The extinction difference required for the calculation of the lactate concentration is obtained after subtraction of the extinction of the blank from the extinction of the sample.

The process according to the present invention is not only simple and quick to carry out but is also characterized by a great degree of exactitute and correctness. The precision in the series amounts to ±2% and that from day to day also ±2%. In control sera, the found lactate content is 99% of the actual value.

A further advantage of the process according to the present invention is the possibility of reducing the consumption of enzymes. Thus, the minimum amount of the rather expensive GPT per ml. of test volume is only 2 U, in comparison with 4 U in the case of the known process. The minimum amount of LDH in the case of this amount of GPT is 30 U/ml.

The present invention also provides a reagent for carrying out the above-described process which comprises LDH, GPT, NAD and glutamate and is characterized by containing 0.40 to 1.2 mol/liter of carbonate buffer of pH 9.5 to 10.5. The buffer substance is preferably used as the Li, Na, K or ammonium salt.

In a preferred embodiment, the reagent according to the present invention contains 0.45 to 1.0 mol/liter carbonate buffer of pH 9.5 to 10.5, as well as 50 – 150 mMol/liter glutamate, 3 – 10 mMol/liter NAD, 20 – 60 U LDH and 2 to 4 U GPT per ml. of buffer solution.

As stabilizer, the reagent according to the present invention preferably contains 2 to 30 mMol alkali metal azide per liter of buffer solution.

For a single determination, in general there are used 5 ml. of the above-described reagent. In a mixed state, the reagent has, at 4° C., a storage stability of at least one day. In order to achieve a longer storage stability, the enzymes are preferably stored separately and the final reagent is prepared by admixture thereof in each case only for daily needs.

Apart from the determination of L-lactate, the process according to the present invention can also be employed for the determination of L-alanine.

In the latter case, the reactions take place in reverse order, such as is described by H. H. Bergmeyer in "Methoden der enzymatischen Analysis", pub. Verlag Chemie, Weinheim, Vol. II, page 1727/1974. In the case of the known process forming the basis thereof, the determination takes 30 to 60 minutes, depending upon the L-alanine concentration, whereby 10 U GPT must be used per ml. test volume. However, in the case of the process according to the present invention, the reaction time for this purpose can be reduced to one half.

The following example illustrates the present invention:

EXAMPLE 1

5 ml. of a reaction mixture were used which contained 0.5 mol/liter carbonate buffer of pH 10.0, 100 mMol/liter glutamate, 15 mMol/liter sodium azide and 5 mMol/liter NAD.

0.1 ml. serum or plasma or 0.2 ml. whole blood (1 + 1 deproteinized with 1N perchloric acid) were pipetted thereto.

2.5 ml. of this mixture were pipetted off into a second vessel and to this were added 0.05 ml. enzyme solution consisting of 54 – 138 U LDH and 5 to 10 U GPT in 50 μ liters 3.2M ammonium sulphate solution. The rest of the mixture was left in the first vessel. After 10 minutes, the contents of the first vessel (blank) were transferred into a cuvette with 1 cm layer thickness and the extinction was measured at Hg 365 nm, Hg 334 nm or 340 nm. The extinction of the contents of the second vessel (sample) was measured in the same cuvette. The extinction of the blank was substrated from the extinction of the sample.

$$\Delta E = E_{sample} - E_{blank}$$

ΔE was used in the calculation.

When serum or plasma was used as the sample and the extinction measurement was carried out at Hg 365 nm, the calculation was as follows:

$$m\text{Mol lactate/liter} = \frac{\Delta E \times 52.02 \times 1000}{3.4 \times 10^3}$$

When whole blood was used, after deproteinization, the calculation was as follows:

$$m\text{Mol lactate/liter} = \frac{\Delta E \times 49.06 \times 1000}{3.4 \times 10^3}$$

52.02 and 49.06, respectively, is the dilution factor of the sample in the determination batch.

$3.4 \times 10^3$ cm$^2$/mMol is the extinction coefficient of NADH at Hg 365 nm.

EXAMPLE 2

The following was pipetted into a cuvette with 1 cm thickness:

2,50 ml 0,1 Mol/liter tris, 0,5 Mol/liter Na-carbonate buffer, pH = 7,6; 8 mMol/liter sodium azide 0,5 ml sample resp. water 0,10 ml 0,2 Mol/liter oxoglutarate solution 0,05 ml 12 Mol/liter NADH-solution 0,01 ml LDH-solution (5 – 10 U) After 5 min, the absorption $E_1$ was read.

0,02 ml GPT-suspension (10 – 30 U)

After 25 min, the extinction $E_2$ of the sample resp. reagent blank is read.

After deducting the extinction difference ($E_1 - E_2$) of the blank from the extinction difference ($E_1 - E_2$) of the sample, ΔE is obtained for L-alanine. $\Delta E_L$-alanine is used in the calculation.

The calculation is as follows if the measurement was carried out at Hg 365 nm:

$$m\text{Mol L-alanine/l} = \frac{\Delta E \times 54,6 \times 1000}{3,4 \times 10^3}$$

54,6 is the dilution factor of the sample in the determination batch. $3,4 \times 10^3$ cm$^2$/mMol is the extinction coefficient of NADH at Hg 365 nm.

It will be understood that the specification and the example are illustrative but not limitative of the present invention and that other embodiments within the spirit and scope of the invention will suggest themselves to those skilled in the art.

What is claimed is:

1. In a process for the quantitative determination of L-lactate by reaction with nicotinamide-adenine-dinucleotide in the presence of lactate dehydrogenase with the formation of reduced nicotinamide-adenine-dinucleotide and pyruvate, reaction of the latter with glutamate in the presence of glutamatepyruvate-transaminase with the formation of alanine and α-ketoglutarate in alkaline buffered solution and measurement of the reduced nicotinamide-adenine-dinucleotide formed, the improvement comprising carrying out the said reaction in the presence of at least 0.4 mol of carbonate or bicarbonate per liter of buffered solution.

2. Process as claimed in claim 1, wherein the reaction is carried out in a solution which contains 0.45 to 1.0 mol/liter of carbonate buffer.

3. Process as claimed in claim 1, wherein the reaction is carried out at a pH of from 9.5 to 10.5.

4. Process as claimed in claim 1, wherein said reaction solution also contains 2 to 30 mMol alkali metal azide per liter of buffered solution.

5. In a process for the quantitative determination of L-alanine comprising reacting a sample containing L-alanine with a solution composed of an alkaline buffer, reduced nicotinamide-adenine-dinucleotide, oxoglutarate and lactate dehydrogenase; measuring the absorbtion of the solution, reacting the solution with glutamate-pyruvate-transaminase, measuring the absorbtion of the solution, then determining the alannine concentration from the difference in the absorbtions, the improvement comprising carrying out the reactions in the presence of at least 0.4 mol of carbonate or bicarbonate per liter.

6. Reagent for the quantitative determination of L-lactate, which comprises lactate-dehydrogenase, glutamate-pyruvate-transaminase, nicotinamide-adenine-dinucleotide and glutamate and is characterized by a content of 0.40 to 1.2 mol/liter carbonate buffer of pH 9.5 to 10.5.

7. Reagent as claimed in claim 6, which comprises 0.45 to 1.0 mol/liter carbonate buffer of pH 9.5 to 10.5, as well as 50 - 150 mMol/liter glutamate, 3 - 10 m/Mol/liter nicotinamide-adenine-dinucleotide and 20 to 60 U lactate dehydrogenase and 2 to 4 U glutamate-pyruvate transaminase per ml. of buffer solution.

8. Reagent as claimed in claim 6, which additionally contains 2 to 30 mMol alkali metal azide per liter of buffer solution.

* * * * *